United States Patent [19]

Tournier et al.

[11] Patent Number: 5,833,948
[45] Date of Patent: Nov. 10, 1998

[54] BLOOD-POOL IMAGING COMPOSITION COMPRISING MICELLES CONTAINING A LIPOPHILIC CHELATING AGENT AND A NON-IONIC SURFACTANT

[75] Inventors: Hervé Tournier, Valleiry, France; Bernard Lamy, Geneva, Switzerland; Roland Hyacinthe, Douvaine, France

[73] Assignee: Bracco Research S.A., Switzerland

[21] Appl. No.: 663,545

[22] Filed: Jun. 13, 1996

[30] Foreign Application Priority Data

Jun. 15, 1995 [CH] Switzerland .................. 958104036

[51] Int. Cl.$^6$ .................................................. A61B 5/055
[52] U.S. Cl. .................. 424/9.321; 424/9.32; 514/836; 514/937
[58] Field of Search ................. 424/9.321, 9.36, 424/9.364, 9.32, 9.322; 128/653.4, 654; 436/173; 514/836, 937

[56] References Cited

U.S. PATENT DOCUMENTS

| | | | |
|---|---|---|---|
| 4,728,575 | 3/1988 | Gamble et al. ................. | 424/9.321 |
| 5,215,680 | 6/1993 | D'Arrigo ........................ | 252/307 |
| 5,312,617 | 5/1994 | Unger et al. .................... | 424/9 |
| 5,387,410 | 2/1995 | Bosworth et al. ............... | 424/9.321 |
| 5,534,241 | 7/1996 | Torchilin et al. ................ | 424/9.321 |
| 5,567,410 | 10/1996 | Torchilin et al. ............... | 424/9.4 |

FOREIGN PATENT DOCUMENTS 0160552  11/1985  European Pat. Off. .
WO 94/04197  3/1994  WIPO .

OTHER PUBLICATIONS

*Magnetic Resonance in Medicine*, vol. 27, No. 1, Tilcock et al: "The Design of Liposomal Paramagnetic MR Agents: Effect of Vesicle Size Upon the Relaxivity of Surface–Incorporated Lipophilic Chelates," pp. 44–51.

*J. Liposome Res.* (1994), pp. 837–855, Schwendener: "Liposomes as carriers for paramagnetic gadolinium chelates as organ specific contrast agents for magnetic resonance imaging (MRI)".

*Chemical Abstracts*, vol. 110, No. 17, 24 Apr. 1989; Schwendener et al: "Small unilamellar lipsomes as magnetic resonance contrast agents loaded with paramagnetic manganese–, gadolinium–, and iron–DTPA–stearate complexes".

*Primary Examiner*—Gary E. Hollinden
*Attorney, Agent, or Firm*—Nixon & Vanderhye

[57] ABSTRACT

The invention concerns NMR imaging contrast compositions comprising magnetically responsive species coupled to physiologically acceptable amphipatic organic substrate materials in the form of mixed micelles suspended or dispersed in a physiologically acceptable aqueous liquid carrier. The compositions are particularly useful for diagnostic investigations of the blood-pool. The invention also concerns the preparation of the mixed micelles, as well as of injectable compositions containing the mixed micelles as contrast agents for MRI purpose.

Once injected, the mixed micelles of the compositions behave as imaging contrast enhancers, e.g. they will improve the quality and resolution of the electronically processed images obtained during MRI examinations of the circulation and/or circulation targeted organs. The compositions are formulated to protect the particles of the contrast agents from early removal by the reticulo-endothelial (RES) system of the liver and the spleen, so that they will stay in the circulation for a time sufficient to properly image the blood vessels and to be transported to selected organs. MRI imaging of the circulation and of targeted organs can strongly assist in diagnosing possible ailments in human and animal patients.

27 Claims, 7 Drawing Sheets

SURFACTANT

PHOSPHOLIPID

Gd-CHELATE

BLOOD-POOL IMAGING COMPOSITION COMPRISING MICELLES CONTAINING A LIPOPHILIC CHELATING AGENT AND A NON-IONIC SURFACTANT

TECHNICAL FIELD

The invention relates to NMR imaging contrast compositions comprising a paramagnetic metal ion coupled to a chelating agent having a lipophilic moiety and one or more amphipatic organic compounds. The invention also concerns the preparation of the compositions, as well as injectable MRI blood pool contrast agents, their use and a kit comprising dry contrast composition and a physiologically acceptable aqueous carrier.

BACKGROUND ART

In general, the relatively low molecular weight magnetically responsive water-soluble metal complexes such as Gd-DTPA, Gd-DOTA etc. are not suitable for use as contrast agents for blood-pool imaging due to their partial leakage through the vessel walls (extravasation into the extravascular space) and their very rapid elimination through the kidneys. The rapid elimination renders these substances unsuitable for imaging of the vascular system since they cannot provide acceptable contrasts (decrease of $T_1$ relaxation time of protons) for a sufficient time.

Various attempts to produce substances suitable as MRI contrast agents for blood-pool investigations have been made. Search for contrast agents with long residence times in the blood circulation, high relaxivity and complete elimination of substances administered have brought proposals in which paramagnetic substances are encapsulated into liposome vesicles or immobilised in the liposome membrane, copolymerised with polyethylene glycol or grafted on a polymeric chain such as albumin, dextran or polylysine. Examples of such compositions are Gd-DTPA-albumin, Gd-DTPA-dextran or Gd-DTPA-polylysine complex molecules (see for example: M. D. Ogan et al., Invest. Radiol. 22 (1987) 665; S. C. Wang et al., Radiology 175 (1990) 483; G. Schumann-Giampieri et al., Invest. Radiol. 26 (1991) 969; and A. V. S. Vexler et al. Invest. Radiol. 29 supl. 2 (1994) S62; B. T. S. Dessler et al., Invest. Radiol. 29 supl. 2 (1994) S65; C. D. Meyer et al., Invest. Radiol. 29 supl. 2 (1994) S90; D. D. Shen et al., Invest. Radiol. 29 supl. 2 (1994) S217). The aforementioned compositions exhibit longer dwelling times in the blood than the water-soluble metal complexes, however, their residence times in the circulation are still not sufficient and some of these compounds have shown unacceptable levels of toxicity for blood-pool imaging. Longer residence times and lower immunogenicity have been reported by A. A. Bogdanov et al., Radiology 187 (1993) 701 for Gd-DTPA-MPEG-polylysine complexes which consist of a methoxy poly (ethylene glycol)-shielded macromolecular backbone (polylysine) bearing covalently attached Gd-DTPA.

Among the many approaches for enhancing the relaxivities of paramagnetic substances in the blood, of interest may be the proposal made in WO-A-91/14178 (Research Corporation). This document discloses paramagnetic contrast enhancing agents which are lipophilic in nature and are based on polyaminopolycarboxylic acid derivatives especially EDTA and DTPA derivatives having one or two fatty acid moieties and a carboxymethylacetamide replacing at least one acetic acid group and preferably two acetic acid groups. The preferred paramagnetic metal ions are the usual paramagnetic metal ions including gadolinium. Conjugates of the paramagnetic contrast agents with other physiological agents such as proteins, peptides, antibodies or liposomes have also been disclosed. The lipophilic paramagnetic agents can be incorporated into liposome membrane to assist targeting and improve the relaxivity.

Notwithstanding, the half-life of contrast agents containing paramagnetic species bonded to macromolecules is often too short to be convenient for blood-pool imaging. In order to solve this difficulty, the use of suspensions of liposomal microvesicles containing encapsulated paramagnetic chelates as carriers of NMR contrast agents has been proposed. Use of liposomes for carriers has been proposed for relative biocompatibility and ease of preparation of liposomes and their suspensions. Encapsulation of known paramagnetic contrast agents into liposomes has been described in a number of different publications (e.g. E. C. Unger et al. JMRI 3 (1993), 195–198, EP-A-0 160 552, etc.).

Unfortunately, the useful life of liposome encapsulated contrast agents injected in the circulation is short because of the rapid physiological removal due to opsonization followed by phagocytosis. The opsonization process involves the coating of "intruder" particles by proteins, called opsonins, recognisable by macrophages followed by their removal (phagocytosis) and metabolization of the coated (opsonized) particles by the Kupffer cells of the liver and the spleen.

Hence, liposomes as carriers of water-soluble paramagnetic chelates do not constitute an ideal solution to paramagnetic blood pool contrast agents. As said before most liposomes are subject to rapid removal from the circulation by the liver and the spleen and, although this property may be advantageous for imaging the latter organs, it is strongly undesirable when one wishes to keep the concentrations of contrast compounds in the blood at a relatively high level for a more extended time. Remedies have been proposed to prolong the life of liposomes vesicles in the blood, namely to incorporate protective substances in the vesicle forming lipids. Along this line of approach, "stealth factors", for instance covalently modified lipids, i.e. lipids (phosphatidylethanol amine (PE)) carrying grafted thereon externally extending polyethylene glycol (PEG) segments have been proposed. Also, the incorporation, as "stealth" factors, to the vesicle forming lipids of products such as palmitoylglucuronic acid (PGlcUA) has been reported to improve the half-life of liposomes in the blood.

It is well known that the lifetime of liposomes in the blood may be significantly prolonged by making the liposome vesicles very small e.g. 50 nm or less. The suggestion is based on the fact that small particles are less size-recognisable by opsonins; therefore if the vesicles are sufficiently small, their residence time in the blood will increase. The trouble with very small vesicles, however, is that with reduction in size their entrapment capacity becomes very small which is not compatible with the amounts of contrast media required for imaging the blood-pool with paramagnetic compounds. Another drawback of liposomes is that the presence of the lipid membrane markedly shields the action of the contrast agent on the water protons within the investigation site. Although this negative effect can be reduced by incorporating the contrast agent within the membrane lipids, for instance by grafting a lipophilic group to the chelatant of the contrast agent (see R. A. Schwendener et al. Internat. J. Pharm. 49 (1989), 249–59), the results have been still insufficient up to now, the ratio of magnetically active substance to substrate being still relatively low and the residence time in the blood relatively short.

Hence the residence time of known paramagnetic MRI contrast agent compositions is still insufficient which renders these agents relatively ineffective when organ perfusion and blood volume measurements/imaging are required. Furthermore, although the longitudinal relaxivity $r_1$ or ($1/T_1$) of the known agents is acceptable, further increase of this factor could provide even better contrast and resolutions, hence better imaging and/or would provide more effective agents requiring administration of lower amounts of imaging substances for the same quality and image resolution. Lowering the amount of the contrast agent administered would lead to even lower level of toxicity. Thus, providing a paramagnetic blood-pool contrast composition/agent which has a substantive action on the relaxation time $T_1$ of water protons, sufficient stealth properties for blood-pooling i.e. a life-time sufficient for effecting complete imaging with only one dose of injected composition, together with a very low or no immunogenicity and an optimal mole ratio of MRI responsive substance to pharmaceutically acceptable organic substrate is still very desirable in order to minimise possible after-injection side-effects.

SUMMARY OF THE INVENTION

In brief, the invention relates to the paramagnetic, MRI responsive contrast compositions comprising in a suitable aqueous carrier liquid, a paramagnetic metal ion, a chelating agent having a lipophilic moiety, and a physiologically acceptable non-ionic surfactant or a mixture of non-ionic surfactants. Optionally, the composition may include one or more amphipatic compounds e.g. phospholipids. The chelating agent comprises a polyaminopolycarboxylate backbone carrying at least one lipophilic substituent e.g. an ester of a fatty alcohol. Complexes of paramagnetic metal ions with the chelating agents are referred to as the imaging agents. The compositions of the invention are associations of imaging agents, non-ionic surfactants, and optionally phospholipids, into stable mixed micelles suspended in a suitable carrier liquid. The mixed micelles are constituted by conjugation or association of the imaging agent with non-ionic surfactant and optionally an amphipatic compound. The term association or conjugation means that the components of the micelles may be in the form of adducts or admixtures of two or more substances having mutual affinity; or the association may be due to one or more bonds e.g. H-bonds between the constituents, whereby a chelatant molecule with simultaneous lipophilic and hydrophilic properties will be provided in a given desirable equilibrium (appropriate hydrophilic/lipophilic balance). Hence, the imaging composition may comprise a mixture of a substrate having suitable amphiphilic properties, and a compound including a paramagnetic species and a function possessing affinity for the substrate; or the imaging composition may comprise a more or less loose adduct of the foregoing constituents.

Clearly, the presence of the non-ionic surfactant or mixtures of non-ionic surfactants in the composition is essential since the non-ionic surfactant causes the principal constituents i.e. the paramagnetic metal ion and the chelating agent having a lipophilic function, the phospholipid and the surfactant to form mixed micelles. By rendering the principal constituents of the composition micellar the properties of the constituents change and unexpectedly effective imaging properties are obtained. The size of the micelles is found to vary between 10 and 800 nm, however, it appears that the most effective results are obtained when the size is preferably between 30 and 500 nm. Dispersed in a suitable aqueous carrier liquid, the mixed micelles form very stable colloidal dispersions which resist agglomeration or aggregation for a long period.

The invention also relates to a method of making the paramagnetic contrast compositions comprising non-ionic surfactants, their use as blood pool contrast agents, and a method of manufacture of contrast agents as dry powders obtained by lyophilisation of the composition.

A kit comprising a vial with dry pulverulent formulation obtained by lyophilisation of the composition and optionally a vial with an aqueous physiologically acceptable carrier is also disclosed.

DETAILED DESCRIPTION OF THE INVENTION

The main aspects of the invention as set out in the accompanying claims are based on an unexpected finding that exceptionally effective paramagnetic NMR contrast compositions are obtained when in addition to a paramagnetic metal ion complexed with a polyaminopolycarboxylate chelating agent having a lipophilic moiety, the imaging composition comprises a physiologically acceptable non-ionic surfactant or a mixture of non-ionic surfactants and preferably one or more amphipatic compounds such as phospholipids. The paramagnetic metal ion is complexed with the polyaminopolycarboxylate and the complex is often referred to as imaging agent. This notwithstanding that only paramagnetic ion has the desired magnetic properties and is therefore almost solely responsible for the imaging action i.e. change in relaxivity of the hydrogen atoms of water. The complexing of the metal ion and hence the presence of the chelating agent is required only to counteract the toxicity of the paramagnetic metal ions and eliminate their undesired effects. Amongst chelating agents derivatives polyaminopolycarboxylic acids are found to be particularly useful for complexing the paramagnetic ions intended for NMR imaging of human or animal body.

In the compositions according to the invention, the polyaminopolycarboxylate chelating agent is provided with a hydrophobic group (for instance, an esterified fatty alcohol chain) which readily couples or intertwines (presumably by Van der Waals forces) with the hydrophobic part of non-ionic surfactant and optionally with the fatty acid residues of the phospholipid. The non-ionic surfactant presumably provides the additional hydrophilic/lipophilic balance parameters to enable the four component system to exist as mixed micelles dispersed in a carrier liquid.

Figure 1:
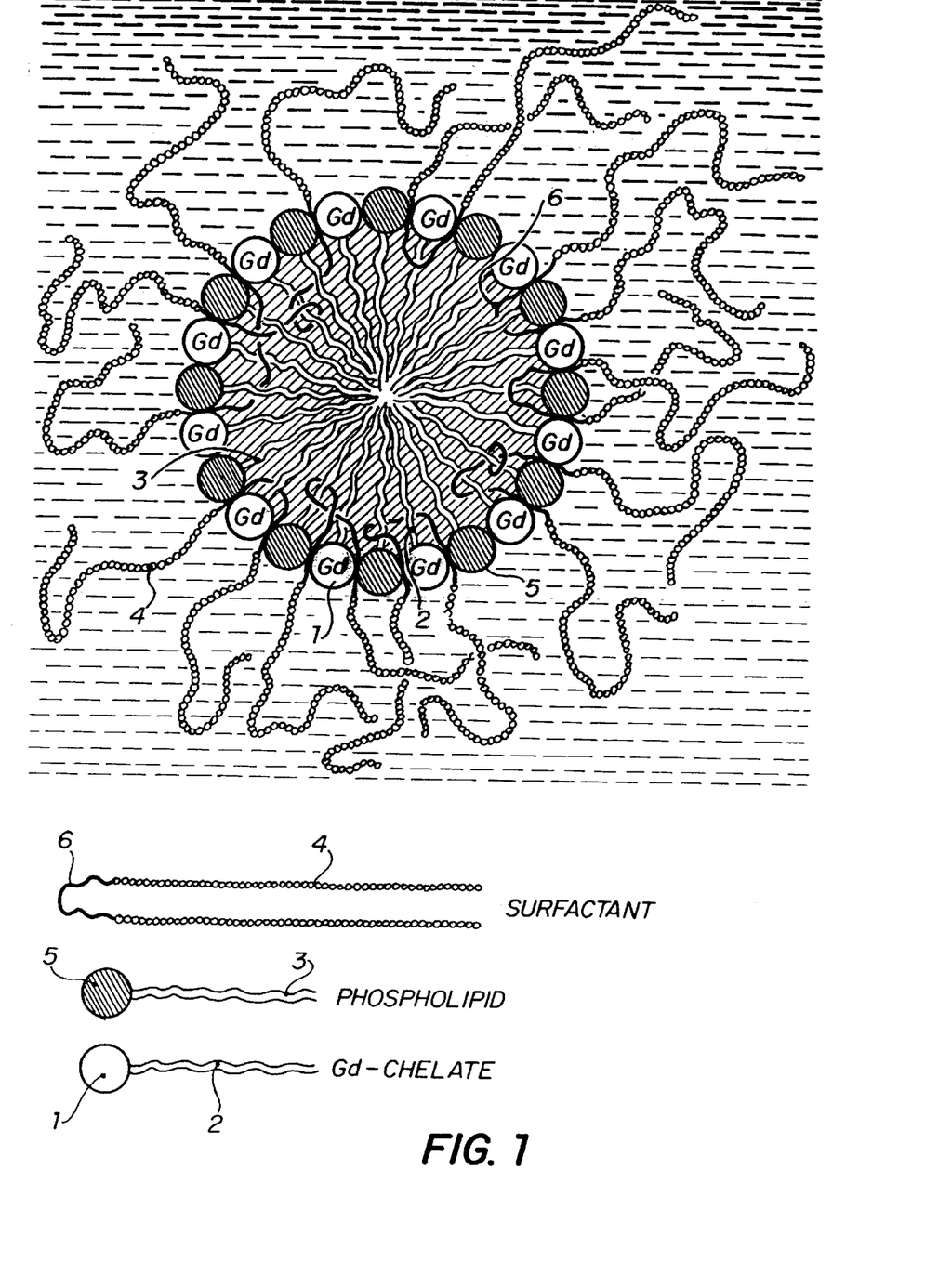
FIG. 1 is a schematic presentation of a mixed micelle of the composition comprising a paramagnetic metal ion 1, a chelating agent having a lipophilic moiety 2, a phospholipid 3 and a physiologically acceptable non-ionic surfactant 4.

As schematically presented in FIG. 1, said mixed micelles comprise a paramagnetic metal ion (1) retained by a chelating agent having a lipophilic moiety (2), an amphipatic compound e.g. a phospholipid (3) and a non-ionic surfactant (4). This configuration of a paramagnetic metal ion bonded to an amphipatic structure i.e. a polyaminopolycarboxylate segment comprising ionic hydrophilic functions, a non-ionic hydrophilic function (the polyethylene oxide segment) and non-ionic hydrophobic aliphatic chains has shown strikingly high contrast efficiency in NMR blood pool imaging. As it may be seen from the experimental part, this contrast effect is at least 30% better than that of comparative compositions of the prior art in which the phospholipid is laminar (vesicular form) instead of micellar. The exact reason why this configuration difference is so effective is still unexplained; however, it has been established that the mixed micelles may have particle sizes between 10 and 800 nm, best results being obtained with the micelles of size in the range between 30 and 500 nm.

Figure 2:
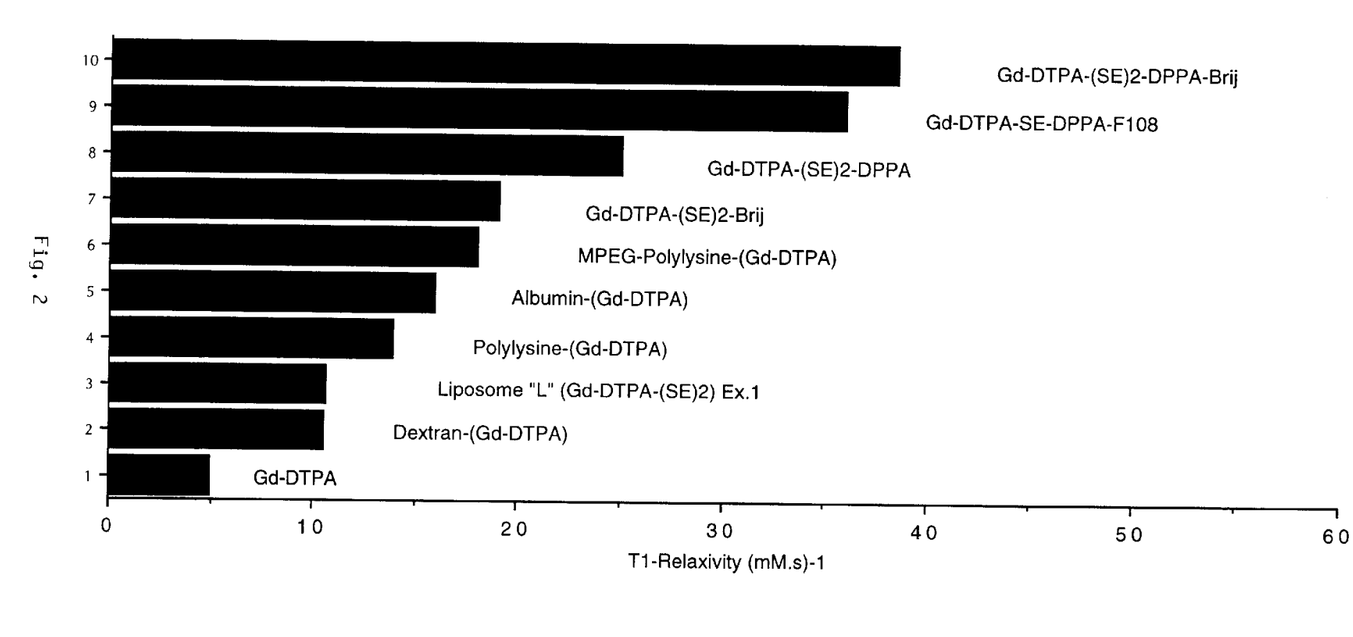
FIG. 2 is a graph showing comparative data of $T_1$-Relaxivity in water obtained for Gd-DTPA, various Gd-based macromolecular agents and the micellar Gd-DTPA-SE/DPPA/F108, Gd-DTPA-(SE)$_2$/DPPA/BRIJ®78 and Gd-DTPA-(SE)$_2$/BRIJ®78 compositions according to the invention.

A possible explanation of the exceptional properties of the mixed micelles of the invention and their suitability as MRI blood-pool contrast agents may come from the fact that they have simultaneous affinity for water and for oils, i.e. they possess suitable lipophilic/hydrophilic balance. The hydrophilic functions involved are ionic and non-ionic. The corresponding hydrophilic/lipophilic balance (HLB) may vary considerably and may be between 1 to 50, but is preferably from 5 to 15. It is speculated that due to these equilibrated surfactant properties, when the mixed micelles are dispersed in a suitable aqueous carrier liquid, they form very stable colloidal dispersions, i.e. the micelles resist agglomeration or aggregation into larger aggregates for a long period. The diagram presented in FIG. 2 shows relaxivity values $T_1$ obtained for the contrast compounds according to the invention and relaxivity values reported for Gd-DTPA and various Gd-based macromolecular agents. As it can be seen from this comparative diagram, the contrast agents comprising paramagnetic contrast composition in the form of mixed micelles provides relaxivities which are 30–250% greater than that of the heretofore known compositions. Thus, the higher relaxivities coupled to the longer residence times in the circulation obtained with the paramagnetic contrast agents of the invention provide an important advance (advantage) in comparison to the known NMR contrast agent compositions.

The mixed micelles according to the invention may be produced using non-ionic, ionic and mixtures of ionic and non-ionic surfactants however, due to their physiological suitability the non-ionic surfactants are preferred. The non-ionic surfactants are preferably block-copolymers having polyoxyethylene and polyoxypropylene segments, polyethyleneglycol-alkylethers such as for example polyethyleneglycol-octadecylether, or polyoxyethylene fatty acid esters, or polyoxyethylene sorbitan fatty acid esters, or n-alkyl glycopyranoside and n-alkyl maltotrioside. The non-ionic surfactant in the compositions of the invention is conveniently selected from the commercially available products such as Pluronic®, Poloxamer®, Poloxamine®, Synperonic®, BRIJ®, Myrj®, Tween®s (polysorbates) and their mixtures. The weight proportion of the surfactant relative to the amount of the paramagnetic imaging agent is from 1:50 to 50:1, preferably 1:10 to 10:1, and even more preferably 1:1.

In order to make the imaging polycarboxylic chelating molecule compatible with the phospholipids and the non-ionic surfactants, the chelating molecule is provided with a hydrophobic group, for instance in the form of carboxylate ester with hydrophobic aliphatic or aromatic alcohols. As said alcohols, one may cite saturated and unsaturated $C_1$ to $C_{24}$ alcohols like methanol, ethanol, propanol, butanol (n-, iso-, tert-), pentanol, hexanol (and isomers), heptanol, octanol (and isomers), nonanol, decanol and fatty alcohols; as aromatic alcohols, one may cite substituted and unsubstituted benzyl- and higher phenylalkyl-alcohols. The chelating molecule may also be provided with the hydrophobic group in form of a carboxylate amide with hydrophobic aliphatic or aromatic amines. Said amines may be saturated and unsaturated $C_1$ to $C_{24}$ amines like methylamine, ethylamine, propylamine, butylamine (n-, iso-, tert-), pentylamine, hexylamine (and isomers), octylamine (and isomers), nonylamine, decylamine, aminoadamantan and fatty amines; as aromatic amines, one may cite substituted and unsubstituted benzyl- and higher phenylalkyl-amines. Alternatively, the polycarboxylic chelating agent can be provided with lipophilic hydrophobic groups linked to the alkylene segments of the molecular back-bone, or to the α-carbon of the carboxylate functions or to a hydroxyl group when present in the chelating agent. An example of the latter is the product of reaction between Gd-HP-DO3A with a fatty acid chloride.

Experiments have shown that the lipophilic moiety of the polyaminopolycarboxylate chelating agent may vary in the range from a methyl ($C_1$) to a long chain alkyl or alkylene group with as many as 24 carbon atoms ($C_{24}$) and may also include substituted or unsubstituted benzyl- or higher phenyl alkyl groups. In fact as long as the polycarboxylic chelate has a lipophilic function which presumably provides an anchor for the phospholipid and/or the surfactant molecules the mixed micelles are formed. The mixed micelles obtained seem reasonably stable even with short alkyl groups however for merely practical reasons alkyl groups with $C_{12}$–$C_{18}$ are preferred. It has been found that when the non-ionic surfactant is eicosaethyleneglycol-octadecylether known under its trademark of BRIJ® 78 the presence of the phospholipid although beneficial in view of higher relaxivity is not really necessary, as the micelles of the surfactant and the paramagnetic complex are showing acceptable relaxivity and reasonable stability in the circulation.

The amphipatic compounds suitable in the present composition are phospholipids which may be selected from phosphatidic acid (PA), phosphatidylcholine (PC), phosphatidylethanolamine (PE), phosphatidylserine (PS), phosphatidylglycerol (PG), phosphatidylinositol (PI), cardiolipin (CL) and sphingomyelin (SM). The amphipatic compound may also consists of a mono-phosphate ester of a substituted or partially substituted glycerol, at least one functional group of said glycerol being esterified by saturated or unsaturated aliphatic fatty acid, or etherified by saturated or unsaturated alcohol, the other two acidic functions of the phosphoric acid being either free or salified with alkali or earth-alkali metals. Preferably the phosphate esters will include monophosphates of fatty acid glycerides selected from dimyristoylphosphatidic acid, dipalmitoylphosphatidic acid, or distearoylphosphatidic acid.

The phospholipids may also include diacyl and dialkyl glycerophospholipids in which the aliphatic chains have at least twelve carbon atoms, as well as one or more compounds selected from ionic and neutral phospholipids, mono alkyl or alkenyl esters of phosphoric acid and/or cholesterol, ergosterol, phytosterol, sitosterol, lanosterol, and tocopherol. In the compositions containing phospholipids, the weight proportion of the phospholipids to the polycarboxylic acid chelate seems not critical and it may vary in a wide range e.g. from 1:50 to 50:1. The practical range will be between 10:1 and 1:10, preferably between 1:5 and 5:1 and even more preferably between 1:3 and 3:1 this since the use of a large excess of chelate may result in unnecessary waste of the chelating/imaging agent while an excess of phospholipid beyond certain concentration does not provide extra benefit. In the compositions in which phospholipids are used the weight ratio of the phospholipid to the surfactant may vary as above, however the ranges from 1:10 to 10:1 and preferably between 1:2 and 2:1 are considered as the ranges in which optimal compositions of the NMR blood pool agent are to be found.

The chelate moiety of the magnetically responsive component of the present nicelles may be selected from EDTA, DTPA, BOPTA, DOTA, DO3A and/or their derivatives, and the paramagnetic metal may be selected amongst well known group of paramagnetic metals notably from Gd(III), Mn(II), Cr(III), Cu(II), Fe (III), Pr(III), Nd(III) Sm(III), Tb(III), Yt(III) Dy(III), Ho(III) and Er(III).

It has also been established that a very useful form of the composition according to the invention may be produced by lyophilisation of the composition whereby a dry, pulverulent formulation is obtained. This form of the paramagnetic composition is particularly convenient for long term storage. The storage in the powder form is simplified by the fact that reconstitution of the composition comprising mixed micelles is achieved by dispersion of the lyophilised powder in a physiologically acceptable liquid carrier, will form a suspension useful as a blood pool NMR imaging contrast agent. Ihe lyophilisation is a straight forward freeze-drying process requiring no particular precautions or measures.

The method for making compositions according to the invention comprises selecting as components a paramagnetic contrast agent with an appropriate polycarboxylic acid chelating agent provided with a suitable lipophilic group in admixture with one or more phospholipids and non-ionic surfactants and dispersing the components into micellar form in a physiologically acceptable aqueous liquid carrier such as water or saline, neat or buffered, according to usual practice. Depending upon the choice of components, the dispersion can be achieved by gentle mixing or by more energetic means such as homogenisation, microfluidization or sonication.

In an advantageous mode of performing the above preparation using for instance, as the required components, the mono- or di-stearyl ester of gadolinium DTPA, dipalmitoylphosphatidic acid (DPPA) as the phospholipid, and Synperonic® F-108 as a non-ionic surfactant, one part by weight of the contrast component is admixed with two parts each of the lipid and the surfactant, and 100 to 200 parts of water. The mixture is homogenised by sonication at a temperature of 50°–80° C. for a few minutes, until the dispersed mixtures forms mixed micelles mostly in the range of 20–250 nm. Generally, the micelles sizes distribution is Gaussian.

Alternatively, two components of the present particulate adduct, for instance the paramagnetic imaging component and the phospholipids, can be first dispersed in the aqueous carrier liquid and the third component added afterwards to the dispersion, whereby the addition of said third component will cause the dispersion to become into micellar form.

Hence, in an advantageous mode of carrying out this alternative, one part by weight of the paramagnetic component and two parts of the phospholipid are dissolved in a suitable organic solvent such as chloroform, methylene chloride, methanol, or mixtures thereof and the solution is evaporated to dryness under reduced pressure. Then the residual solid is finely dispersed in about 100 to 200 part of water (or other physiologically acceptable liquid carrier), for instance by sonication, microfluidization, or otherwise, about two parts of the F-108 surfactant (or of an equivalent compound) are added and homogenisation is resumed until micelles are formed as disclosed.

Once prepared, the dispersion can thereafter be sterilised by heat as usual and used as such, or it can be further dehydrated for storage, for instance by lyophilization. The dehydrated material in form of a powder from which the MRI contrast agent may be produced by admixing the powder with a portion of carrier liquid and shaking.

Thus, for practically applying the compositions of the invention in the medical field, the dried components and the carrier liquid can be marketed separately in a kit form whereby the contrast agent is reconstituted by mixing together the kit components prior to injection into the circulation of patients.

The first component of the kit i.e. dry power may further be stored under a dry inert atmosphere and the second component, a physiologically acceptable carrier liquid, may further contain isotonic additives and other physiologically acceptable ingredients such as various mineral salts, vitamins, etc.

As already mentioned the reconstituted agent is particularly suitable for use in NMR blood pool imaging of organs in human or animal body. These compositions could facilitate MR angiography and help to assess myocardial and cerebral ischemia, pulmonary embolism, vascularisation of tumours and tumour perfusion.

The following Examples further illustrate the invention.

EXAMPLE 1

Figure 3:
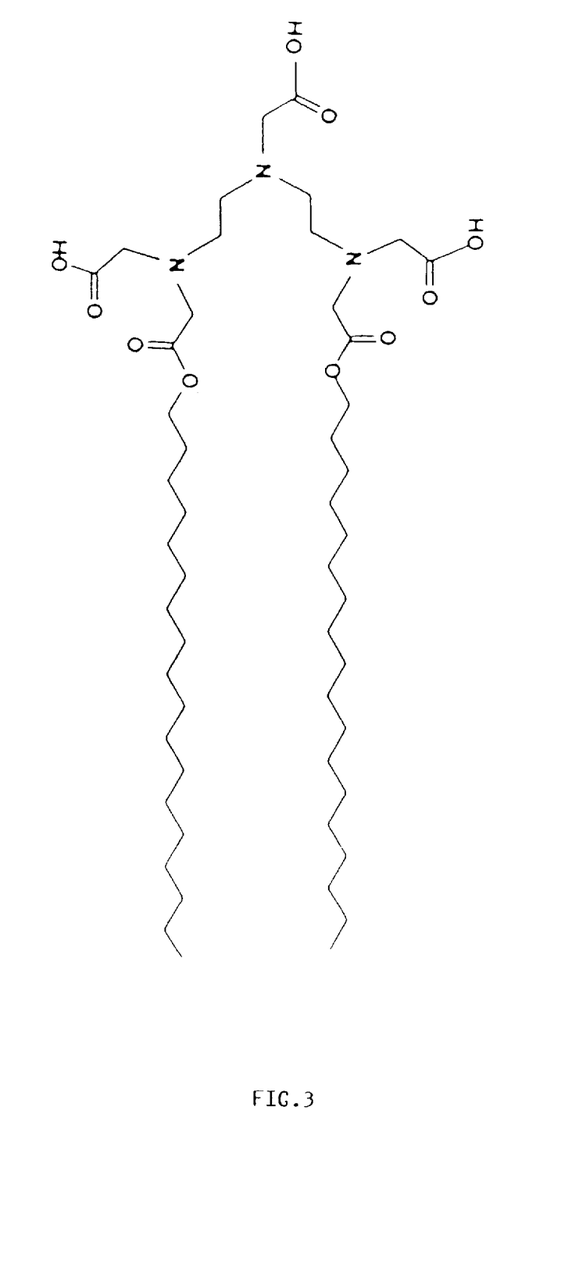
FIG. 3 is a schematic presentation of structural formula of the amphipatic derivative of DTPA [DTPA-(SE)$_2$] prepared via reaction of DTPA anhydride with stearyl alcohol.

The DTPA mono- and di-stearyl esters of formulae, shown in FIG. 3, and the corresponding gadolinium chelates (Gd-DTPA-SE) and (Gd-DTPA(SE)$_2$), were prepared as disclosed in G. W. Kabalka et al., Magnetic Resonance in Medicine 8 (1988), 89–95. The DTPA anhydride required in the synthesis was made according to Eckelman et al., J. Pharm. Sci. 64 (1975), 704–706. The purity of the imaging agents was checked by measuring the gadolinium content by usual means (decomplexing in 2N hydrochloric acid and titrating with EDTA solution; indicator, Xylenol-orange) and gave results substantially near theory.

Six hundred mg of lecithin (SPC-3, Natterman) (0.788 mmol), 60 mg cholesterol (0.158 mmol), and 332 mg Gd-DTPA-(SE)$_2$ (0.315 mmol) were dissolved in 100 ml of a 1/1 mixture of MeOH and CHCl$_3$. The solution was evaporated to dryness under reduced pressure (Rotavapor, 72° C./15 Torr, 1.5 hrs), after which 20 ml of distilled water were added under agitation. The mixture was further homogenised by sonication for about 30 min at 70° C. (Branson Sonifier, output 40), whereby a homogenous milky suspension of liposome vesicles (labelled "L") was obtained.

To 10 ml of the above suspension were added 300 mg of Synperonic® F108 and sonication was resumed for a few minutes, whereby a stable optically clearer suspension of submicronic particles (labelled "M") in micellar form was obtained.

TABLE 1

|     | $r_1$ | $r_2$ |
| --- | --- | --- |
| "L" | 10.6 | 8.6 |
| "M" | 20.6 | 13.2 |

Proton spin relaxivities of the foregoing suspensions were measured using a Minispec PC-120 (Bruker) apparatus, operating under 0.47 Tesla (20 MHz). EDM 510A (EDM= Experiment Definition Module) was used to measure the spin-lattice relaxation time $T_1$ by the "inversion recovery" method. EDM 610A was used to measure the spin-spin relaxation time $T_2$ by the Carr-Purcell-Meiboom-Gill (GPMG) technique. The relaxivities ($r_1$ and $r_2$) given in the Table 1 are expressed as r in $[mMs]^{-1}=1/T$ for a 1 mM concentration.

The foregoing results clearly demonstrate that converting the imaging compound from vesicular to micellar from sharply increases relaxivity and consequently imaging efficiency.

EXAMPLE 2

In a first preparative mode (mode 1), two samples were prepared by admixing together 100 mg of imaging agent, 200 mg of DPPA (dipalmitoylphosphatidic acid Na salt) and 200 mg of Synperonic® F-108 and 20 ml of $H_2O$, then the mixture was sonicated for 30 min at 70° C., (Branson sonifier output 40). In a first sample ("M1"), there was used as the imaging species the monostearylester Gd-DTPA-SE and in the second sample ("M2"), there was used the distearylester Gd-DTPA-(SE)$_2$.

The mean size of the micelles and the micelle size distribution were determined by a Dynamic Light Scattering (DSL) method also known under the name of Photon Correlation Spectroscopy (PSC) using a Nicomp 370 HDL-NPSS apparatus. The particle size distribution (Gaussian) was measured (Nicomp) and found to have a peak at 150–170 nm SD±60–90 nm for both samples.

Two other samples were prepared from the same ingredients but the technique (mode 2) was modified as follows: the imaging species and the lipids were first dissolved in 25 ml of a 2/1 $CHCl_3$/MeOH mixture, the solution was evaporated to dryness as in Example 1, 20 ml of $H_2O$ were added and dispersion was effected by sonication for 20 min, output 20. Then the F-108 was added and sonication resumed for 10 min. The sample with the monoester was labelled "M3", and that with the diester "M4". The particle size distribution was measured and found to have a peak at 70–80 nm SD±30–40 nm for both samples.

The $r_1$ and $r_2$ results are gathered in Table 2:

TABLE 2

|      | $r_1$ | $r_2$ | size in nm |
| --- | --- | --- | --- |
| "M1" | 28.9 | 17.4 | 152 ± 63 |
| "M2" | 23.8 | 18.3 | 170 ± 90 |
| "M3" | 35.7 | 35.1 | 66 ± 36 |
| "M4" | 30.5 | 30.9 | 79 ± 38 |

It is speculated that the higher $r_1$ and $r_2$ values obtained with the mixed micelles according to "mode 2" may come from the fact that the micelles were smaller and had narrower size distribution than in the "mode 1".

EXAMPLE 3

The experiments of Example 2 were repeated, using mode 2 and Gd-DTPA-SE but changing the nature of the phospholipid, i.e. using dipalmitoylphosphatidylglycerol (DPPG) and dipalmitoylphosphatidylcholine (DPPC). Table 3 gives the results obtained in terms of relaxivities $r_1$ and $r_2$ in $(mM.s)^{-1}$.

TABLE 3

| Phospholipid | $r_1$ | $r_2$ | size in nm |
| --- | --- | --- | --- |
| DPPG-Na | 30.2 | 28.6 | 110 ± 50 |
| DPPC    | 27.3 | 26.9 | 99 ± 47 |
| DPPA-Na | 35.7 | 35.1 | 66 ± 36 |

The experiments of Example 2 were repeated, using mode 2 and Gd-DTPA-(SE)$_2$ but changing the nature of the non-ionic surfactant, i.e. using

TABLE 4

| Phospholipid | $r_1$ | $r_2$ | size in nm |
| --- | --- | --- | --- |
| DPPG-Na | 29.4 | 28.8 | 77 ± 27 |
| DPPC    | 21.6 | 21.5 | 36 ± 26 |
| DPPA-Na | 27.4 | 27.7 | 103 ± 31 | eicosaethyleneglycol-octadecylether known under its trademark of BRIJ® 78 (Fluka). The results obtained in this experiment are given in Table 4.

EXAMPLE 4

A composition was prepared using the directions of Example 2, mode (2) in 0.3M glycerol buffer (5 mM phosphate, pH 7.25). This contained per ml 5 mg of Gd-DTPA-SE, 10 mg of DPPA -Na and 10 mg of Synperonic® F-108.

First a calibration curve was constructed by diluting the composition with rat blood to a range of known Gd concentrations and measuring $T_1$ and $T_2$ for each concentration of Gd.

The composition was then injected intravenously into experimental rats (about 200 g) at the dose of 0.0385 mmol of Gd/kg (about 2 ml of suspension/animal). Two rats (making one group) were used in each experiment.

Figure 4:
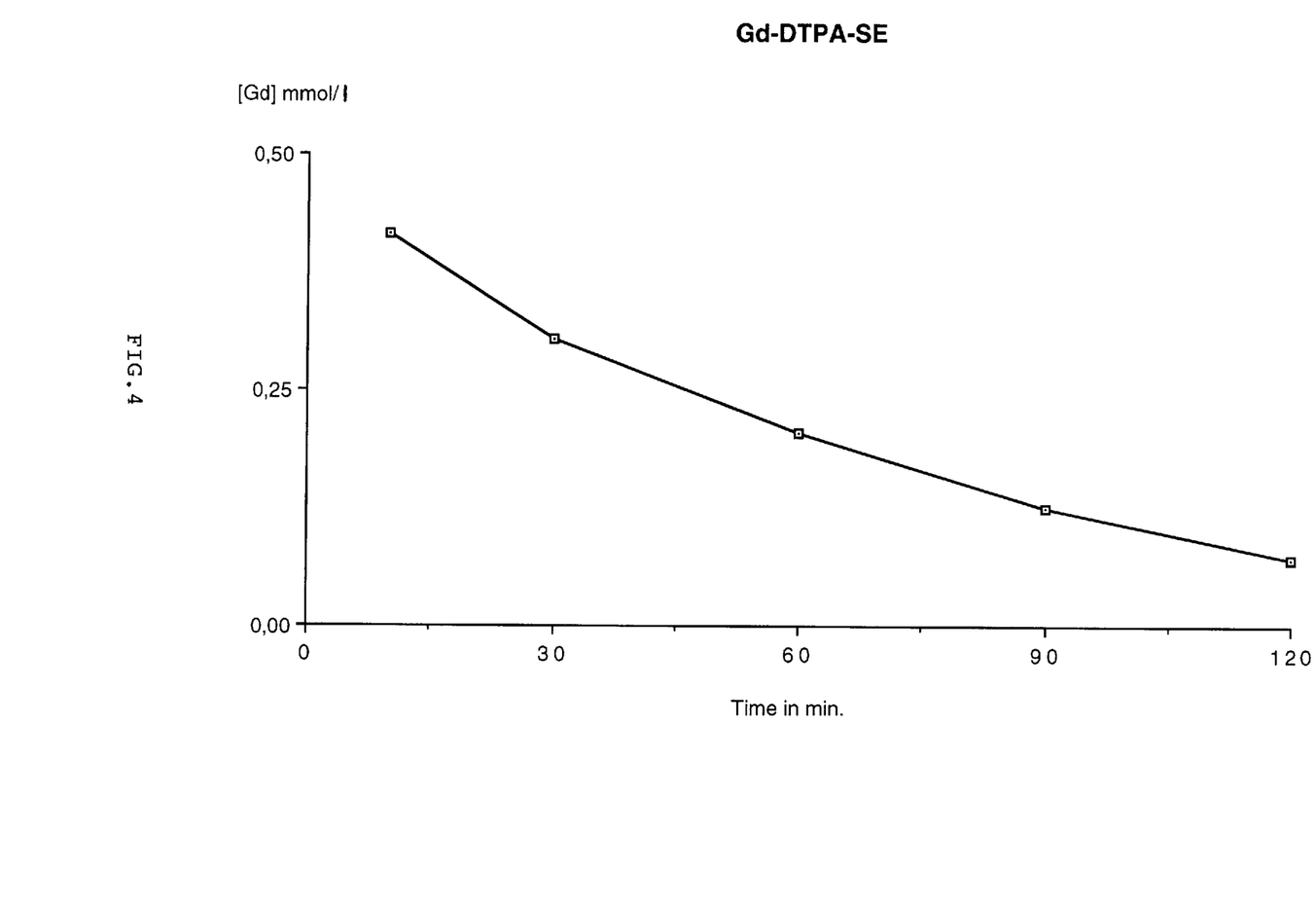
FIG. 4 is a diagram of blood pharmacokinetics in the rat of a micellar Gd-DTPA-SE/phospholipid/F108 composition according to the invention.

NMR relaxation measurements ($T_1$ and $T_2$) were carried out on 5 ml of the blood samples and the values (expressed in terms of Gd concentrations [Gd] by means of the calibration curve) were plotted against time to give the graph of FIG. 4. The best mathematically fitting curve is given by the equation:

$$[Gd](mmol/l)=0.5e^{-0.0157\ t(min)}$$

(showing a one compartment pharmacokinetic model).

The main pharmacokinetic parameters calculated from this one-compartment model were:
Elimination half-life=44 min
Area under curve $[AUC]0-\infty=31.8$ mM·min
Volume of distribution=0.077 l/kg (or 77 ml/kg)
Clearance=0.00121 l/kg·min The elimination half-life (44 min) obtained for the micellar form is much longer i.e. better than that obtained for Gd-DTPA (15 min as $t^{1/2}(\beta)$).

EXAMPLE 5

An injectable composition was prepared according to Example 2, mode (2) using Gd-DTPA-(SE)$_2$ in place of Gd-DTPA-SE.

Figure 5:
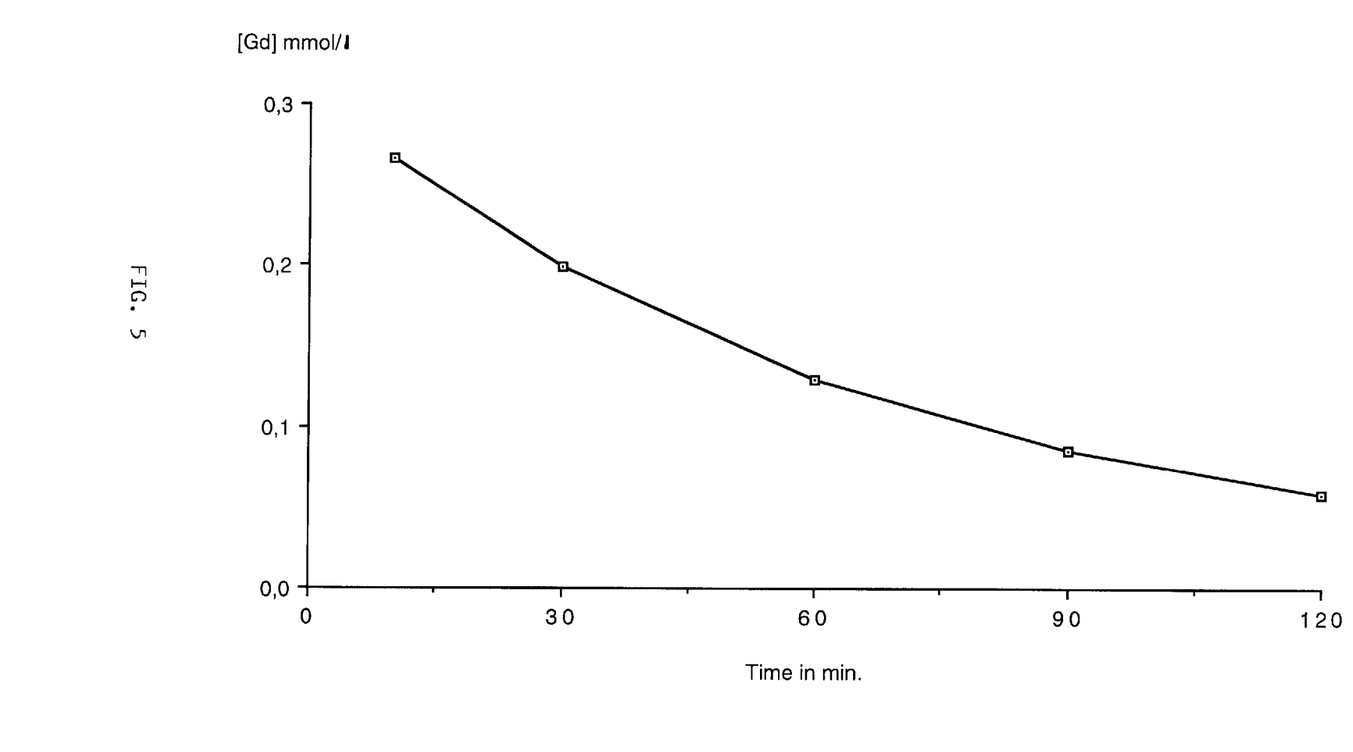
FIG. 5 is a diagram of blood pharmacokinetics in the rat of a micellar Gd-DTPA-(SE)$_2$/phospholipid/F108 composition according to the invention

Then an in-vivo experimental procedure was carried out in the rat as described in Example 4. The injected dose was 0.0345 mmol Gd/kg. The graph of FIG. 5 shows the results obtained.

The expression giving the [Gd] as a function of time was:

$$[Gd](mmol/l)=0.3e^{-0.0138\ t(min)}$$

The main pharmacokinetic parameters were:
Elimination half-life=50 min
Area under curve[AUC]0–∞=21.7 mM·min
Volume of distribution=0.115 l/kg (or 115 ml/kg)
Clearance=0.00159 l/kg·min There was virtually no difference between the results obtained with Gd-DTPA-SE and those obtained with Gd-DTPA-(SE)$_2$.

Much like in the Example 4, the elimination half-life (50 min) obtained for the micelles of the invention is much longer i.e. better than that obtained for Gd-DTPA (15 min as $t^{1/2}(\beta)$).

EXAMPLE 6

Injectable compositions were prepared according to Example 2, mode (2) using $^{153}$Gd radioactive isotope. The following preparations were made:

$^{153}$Gd-DTPA-(SE)$_2$/DPPA Na/Synperonic F-108
$^{153}$Gd-DTPA-(SE)$_2$/DPPG Na/Synperonic F-108
$^{153}$Gd-DTPA-(SE)$_2$/DPPC/Synperonic F-108

The ratio between the components 5:10:10 (mg/ml) was maintained the same for the three preparations.

The $r_1$ and $r_2$ values as well as the mean size distributions were close to the values obtained in Example 3 for the same compounds.

Figure 6:
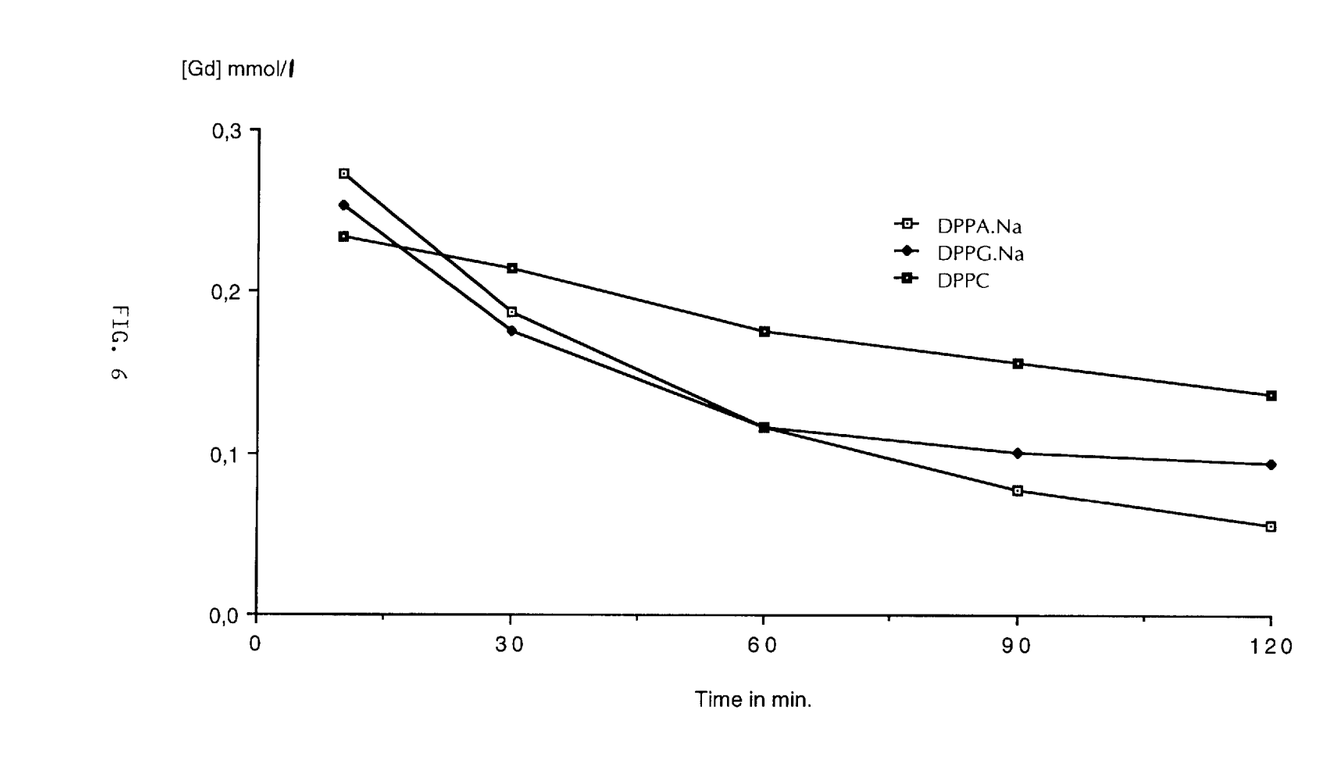
FIG. 6 is a diagram of blood pharmacokinetics in the rat of micellar radio labelled compositions with different phospholipids produced according to the invention.

The preparations were injected into experimental rats (about 200 g) at the dose of 0.0234 mmol of Gd/kg (about 1 ml of suspension/animal) and blood samples taken 10, 30, 60, 90 and 120 min after injection. The experiment was carried out on groups of 3 rats (one group per preparation). The radioactivity of the samples was measured using a γ-counter (Packard Minaxi γ). The change in concentration of Gd in mmol/l in the blood as a function of time for each preparation is shown in FIG. 6.

EXAMPLE 7

Injectable $^{153}$Gd-DTPA-(SE)$_2$/BRIJ® 78 and $^{153}$Gd-DTPA-(SE)$_2$/DPPC/BRIJ® 78 compositions were prepared according to Example 2, mode (1) and mode (2) using $^{153}$Gd radioactive isotope. The weight ratio of the components in the preparations was 5:10 and 5:10:10 respectively.

Figure 7:
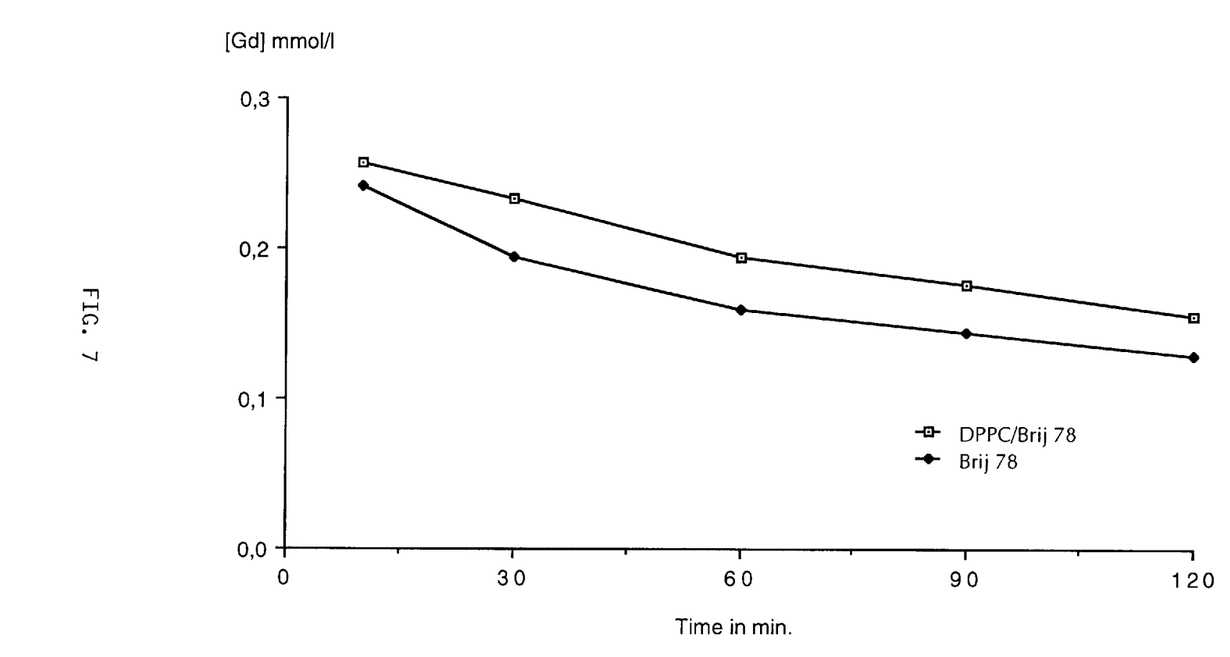
FIG. 7 is a diagram of blood pharmacokinetics in the rat of micellar $^{153}$Gd-DTPA-(SE)$_2$/DPPC/BRIJ® 78 and $^{153}$Gd-DTPA-(SE)$_2$/BRIJ® 78 compositions according to the invention.

The preparations were injected into experimental rats at the dose of 0.0234 mmol of Gd/kg (about 1 ml of suspension/animal) and blood samples taken 10, 30, 60, 90 and 120 min after injection. The radioactivity of the samples was measured using a γ-counter (Packard Minaxi γ). From the plot of change in radioactivity of the samples shown in FIG. 7 it follows that when the preparations are made with BRIJ® 78, the presence of the phospholipid although beneficial in view of higher relaxivity and dwelling time, is not essential since the micelles of the surfactant and the paramagnetic complex are showing reasonably high relaxivity and stability in the circulation.

Relaxivities in (mM.s)$^{-1}$ obtained for the two preparations were:

TABLE 5

|  | $r_1$ | $r_2$ |
|---|---|---|
| DPPC/BRIJ ® 78 | 21.6 | 21.5 |
| BRIJ ® 78 | 18.9 | 17.6 |

It was interesting to note that in the case of $^{153}$Gd-DTPA-(SE)$_2$/BRIJ® 78 preparation the size of the micelles measured was about 538±190 nm i.e. much greater than for the preparations in previous examples.

When the above experiments were repeated with Synperonic® F 108 in place of Brij®, it was found that the compositions obtained were more stable if the phospholipids were present.

EXAMPLE 8

Injectable compositions were prepared according to Example 2, (mode 2) using the following lipophilic chelates:

Gd-DTPA-SA=Gd-DTPA-Stearylamide
Gd-DTPA-(SA)2=Gd-DTPA-Distearylamide
Gd-DTPA-ME=Gd-DTPA-Myristylester
Gd-DTPA-(ME)2=Gd-DTPA-Dimyristylester
Gd-DTPA-OE=Gd-DTPA-Octylester
Gd-DTPA-(Ad)2=Gd-DTPA-Diadamantylamide
Gd-DOTA-SE=Gd-DOTA-Stearylester
Gd-DOTA-PE=Gd-DOTA-Palmitylester
Gd-HP-DO3A-SE=Gd-HP-DO3A-Stearoylester The $r_1$ and $r_2$ values as well as the mean size distribution measured were within the range of values obtained for Gd-DTPA-SE and Gd-DTPA(SE)$_2$ compounds.

FIG. 2 Sources

For Relaxivities of Gd-DTPA, Dextran-(Gd-DTPA), Albumin-(Gd-DTPA) & Polylysine-(Gd-DTPA) see R. C. BRASH Magnetic Resonance in Medicine 22 (1991) 282–287 and for relaxivity of MPEG-Polylyine-(Gd-DTPA) see A. A. Bogdanov et al. Radiology 187 (1993) 701–706.

We claim:

1. An injectable micellar NMR imaging composition comprising as a dispersion in a physiologically acceptable aqueous carrier, a paramagnetic metal ion, a chelating agent having a lipophilic moiety, a physiologically acceptable non-ionic surfactant or a mixture of non-ionic surfactants and optionally one or more additional amphipatic compounds.

2. The composition of claim 1, wherein the micelles are mixed micelles with the particle size between 10 and 800 nm, preferably between 30 and 500 nm.

3. The composition of claim 1, wherein the non-ionic surfactant is a block-copolymer having polyoxyethylene and polyoxypropylene segments, a polyethyleneglycolalkylether, a polyoxyethylene fatty acid ester, a polyoxyethylene sorbitan fatty acid ester, an n-alkylglucopyranoside, or an n-alkyl maltotrioside.

4. The composition of claim 2, wherein the surfactant is Pluronic®, Poloxamer®, Poloxamine®, Synperonic®, BRIJ®, Myrj®, Tween® or mixtures thereof.

5. The composition of claim 1, wherein the surfactant is BRIJ®.

6. The composition of claim 1, wherein the amphipatic compound is a dialkyl glycerophospholipid in which alkyl has at least twelve carbon atoms.

7. The composition of claim 6, wherein the phospholipid is selected from phosphatidic acid, phosphatidylcholine, phosphatidylethanolamine, phosphatidylserine, phosphatidylglycerol, phosphatidylinositol, cardiolipin and sphingomyelin.

8. The composition of claim 7, wherein the phospholipid consists of a mono-phosphate ester of a substituted or partially substituted glycerol, at least one functional group of said glycerol being esterified by saturated or unsaturated aliphatic fatty acid, or etherified by saturated or unsaturated alcohol, the other two acidic functions of the phosphoric acid being either free or salified with alkali or earth-alkali metals.

9. The composition of claim 8, wherein the phospholipid is a monophosphate of a fatty acid glyceride selected from dimyristoylphosphatidic acid, dipalmitoylphosphatidic acid, or distearoylphosphatidic acid.

10. The composition of claim 1, wherein the amphipatic compound comprises two or more compounds selected from ionic and neutral phospholipids, mono alkyl or alkenyl esters of phosphoric acid and/or cholesterol, ergosterol, phytosterol, sitosterol, lanosterol, and tocopherol.

11. The composition of claim 1, wherein the lipophilic moiety of the imaging agent is a $C_1$ to $C_{24}$ alkyl or alkylene group or substituted or unsubstituted benzyl- or phenyl alkyl group.

12. The composition of claim 11, wherein the lipophilic moiety of the imaging agent is a carboxylate ester of saturated and unsaturated $C_1$ to $C_{24}$ aliphatic or aromatic alcohols or is a carboxylate amide of saturated and unsaturated $C_1$ to $C_{24}$ aliphatic or aromatic amines.

13. The composition of claim 12, wherein the alcohol is methanol, ethanol, propanol, butanol (n-, iso-, tert-), pentanaol, hexanol and isomers, heptanol, octanol, nonanol, decanol and isomers, fatty alcohols, substituted and unsubstituted benzyl- and higher phenylalkyl-alcohols.

14. The composition of claim 12, wherein the amine is methylamine, ethylamine, propylamine, butylamine (n-, iso-, tert-), pentylamine, hexylamine (and isomers), heptylamine, octylamine (and isomers), nonylamine, decylamine, aminoadamantane, fatty amines and substituted and unsubstituted benzyl- and higher phenylalkyl-amines.

15. The composition of claim 11, wherein the lipophilic moiety of the imaging agent is provided with lipophilic hydrophobic groups linked to the alkylene segments of the molecular back-bone, to the α-carbon of the carboxylate functions or to a hydroxyl group when present in the chelating agent.

16. The composition of claim 11, wherein the chelate is selected from EDTA, DTPA, BOPTA, DOTA, DO3A and/or derivatives thereof.

17. The composition of claim 16, wherein the paramagnetic metal ion is selected from Gd(III), Mn(II), Cr(III), Cu(II), Fe (Ill), Pr(III), Nd(III) Sm(Ill), Tb(III), Yt(III) Dy(III), Ho(III) and Er(III).

18. The composition of claim 1, wherein the weight ratio of the lipophilic imaging agent and the surfactant in the composition is between 1:10 and 10:1, preferably between 1:3 and 3:1.

19. The composition of claim 6, wherein the weight ratio of the phospholipid to the surfactant is from 1:10 to 10:1 and preferably between 1:2 and 2:1.

20. A dry, pulverulent formulation comprising the composition of claim 1, which upon dispersion in a physiologically acceptable liquid carrier, will form a suspension useful as a blood pool NMR imaging contrast agent.

21. An injectable aqueous suspension comprising the composition of claim 1 suspended in a physiologically acceptable liquid carrier useful as a NMR blood pool contrast agent.

22. A method for making composition of claim 1, characterised by the steps of:
   a) selecting and suspending a complex of a paramagnetic metal ion, a chelating agent comprising a lipophilic moiety, one or more non-ionic surfactants, and optionally one or more amphipatic compounds and in an aqueous phase to form a mixture, and
   b) energising the mixture by sonicating or microfluidizing to bring the ingredients into intimate contact and produce homogeneous dispersion of the components in micellar form.

23. The method of claim 22, wherein after the sonication or microfluidization the mixture is sterilised and/or lyophilised.

24. The method of claim 22, wherein the surfactant is added to the mixture of the compound after said energising and optionally repeating the sonication or microfluidization.

25. The method of claim 22, wherein the amphipatic compound is a phospholipid selected from monophosphate of a fatty acid glyceride selected from dimyristoylphosphatidic acid, dipalmitoylphosphatidic acid, or distearoylphosphatidic acid.

26. The composition of claim 1, for use in NMR blood pool imaging of organs in human or animal body.

27. A two component kit comprising, as the first component, a dry formulation of claim 20 stored under an inert atmosphere and, as the second component, a physiologically acceptable carrier liquid which when admixed with the first component provides, as a suspension of the two components, an injectable NMR contrast composition of claim 1.

* * * * *